United States Patent [19]

Simons, Jr. et al.

[11] Patent Number: 5,215,916
[45] Date of Patent: Jun. 1, 1993

[54] SUPER GLUCOCORTICOID RECEPTORS: RECEPTORS WITH INCREASED AFFINITY AND SPECIFICITY FOR GLUCOCORTICOID STERIODS

[75] Inventors: Samuel S. Simons, Jr., Bethesda; Pradip K. Chakraborti, Rockville, both of Md.; Keith R. Yamamoto; Michael J. Garabedian, both of San Francisco, Calif.

[73] Assignee: The United States of America as represented by the Department of Health & Human Services, Washington, D.C.

[21] Appl. No.: 716,827

[22] Filed: Jun. 19, 1991

[51] Int. Cl.$^5$ .............. C07K 13/00; C12N 15/12; C12N 15/63
[52] U.S. Cl. .............. 435/252.3; 435/69.1; 435/320.1; 530/350; 536/23.5
[58] Field of Search .............. 435/69.1, 172.1; 530/350; 935/9, 13

[56] References Cited

PUBLICATIONS

Miesfeld et al., 1986, Genetic Complementation of a glucocorticaid receptor deficiency . . . cell vol. 46, 389–399.
Miller et al., 1988, Steroid binding to Hepatoma Tissue Culture Cell Placocorticoid Receptors . . . J. Biol. Chem. 263:15217.
Simons et al., 1987, Identification of Cysteine 656 as the amino acid of hepatoma . . . J. Biol. Chem. 262:9676.
Chakraborti et al., 1991, Creation of Super Glucocorticoid Receptors . . . J. Biol. Chem. 266(33):22075.

Primary Examiner—Robert J. Hill, Jr.
Assistant Examiner—John D. Ulm
Attorney, Agent, or Firm—Needle & Rosenberg

[57] ABSTRACT

The present invention relates to novel glucocorticoid receptors that have greater affinity and specifity for glucocorticoid steroids than the naturally occurring receptors. More particularly, the invention relates to the altering of the equivalent of cysteine-656 of the rat glucocorticoid receptor to either serine or glycine for the production of super glucocorticoid receptors which retain full biological activity in intact cells and have higher affinity and specificity for glucocorticoid steroid binding than the original receptor. The invention further relates to the recombinant expression of such altered receptors in host cells.

8 Claims, 1 Drawing Sheet

SUPER GLUCOCORTICOID RECEPTORS: RECEPTORS WITH INCREASED AFFINITY AND SPECIFICITY FOR GLUCOCORTICOID STERIODS

BACKGROUND OF THE INVENTION

1. Field of the Invention

The present invention relates to novel glucocorticoid receptors that have greater affinity and specifity than the naturally occurring receptors. More particularly, the invention relates to the altering of the equivalent of cysteine-656 in the rat glucocorticoid receptor to either serine or glycine for the production of super glucocorticoid receptors which retain full biological activity in intact cells and have higher affinity and specificity of glucocorticoid steroid binding than the original receptor. The invention further relates to the recombinant expression of such altered receptors in host cells.

2. Background Information

The successes of the last several years in cloning the glucocorticoid receptor from several species (S. M. Hollenberg et al., *Nature* 318:635-641 (1985); R. Miesfeld et al., *Cell* 46:389-399 (1986); M. Danielson et al., *EMBO J.* 5:2513-2522 (1986)) have revealed a dramatic conservation in amino acid sequence in the receptors from human, rat, and mouse. The complete sequence for rat glucocorticoid receptor as set forth in R. Meisfeld et al. (1986) is shown in SEQ ID NO. 5. The amino acid sequences of human and rat receptors are 88% identical; this value rises to 92% if one allows for conservative amino acid differences. Likewise the human receptor was found to be 89% homologous with the mouse receptor (Danielson et al., (1986)). Given the extremely high homology between these glucocorticoid receptors, it is not surprising that the human and rat receptors "appear to be operationally indistinguishable" (Miesfeld et al., (1986)).

Steroid binding is the first step in a series of events that translate the structural information of the steroid into the observed biological response. Molecular biology experiments have defined the 250 carboxyl terminal amino acids as being the steroid binding domain of the receptor (V. Giguere et al., *Cell* 46:645-652 (1986); S. Rusconi and K. R. Yamamoto, *EMBO J.* 6:1309-1315 (1987)). In this region, >96% of the amino acid sequence in the human, rat, and mouse receptors is identical. Thus it is not unexpected that the affinity of various steroids for human, rat, and mouse glucocorticoid receptors has been found to be almost identical.

There are separate receptor proteins for each of the five classical steroid hormones—androgen, estrogen, glucocorticoid, mineralocorticoid, and progesterone. Each of these receptors exhibits both a common structural organization of functional domains and appreciable homology between the steroid-binding domains (R. M. Evans, *Science* 240: 889-895 (1988)). This homology offers a reasonable explanation for the fact that virtually all steroids appear to interact with more than one class of receptors (J. -P. Raynaud and T. Ojasoo, In Steroid Hormone Receptors: Structure and Function, (H. Eriksson, and J. -A. Gustafsson, eds.), 141:170 (1983); G. Teutsch et al., *J. Steroid Biochem* 31:549-565 (1988)).

It is possible to achieve total selectivity among the five classical steroid receptors (androgen, estrogen, glucocorticoid, mineralocorticoid, and progesterone) with anti-receptor antibodies. However, selective recognition of the biologically active form of receptors via the binding of specific ligands has been elusive (Raynaud and Ojasoo, 1983; Teutsch et al., 1988). The consequences of such cross-reactivity are manifold. It complicates the identification of the steroid binding form of receptors (S. Lopez et al., *J. Biol. Chem.* 265:16039-16042 (1990)) and causes unwanted side effects in vitro experiments with cells containing the offending receptors. In clinical settings, the side effects can be very severe, such as to limit long term glucocorticoid therapy to only those cases that are not easily remedied by other protocols (G. H. Williams and R. G. Dluhy, In "Harrison's Principles of Internal Medicine." 11th ed. (Braunwald, E., Isselbacher, K. J., Petersdorf, R. G., Wilson, J. D., Martin, J. B., and Fauci, A. S., eds) McGraw-Hill, New York, pp. 1772-1774 (1987)).

One solution to this problem is to use molecular biology to modify the steroid binding domain of the glucocorticoid receptor. An increase in the specificity of steroid binding would be one desirable change. Another would be to increase the affinity of steroid binding, since lowering the concentrations of steroid needed for full glucocorticoid response would also decrease the binding (and lower the biological responses) with other receptors. However, the published reports indicate that this will be very difficult to accomplish. Terminal deletions to give species smaller than amino acids 497-795 (all numbering is for the rat receptor sequence) resulted in more than a 300 fold reduction in affinity (Rusconi and Yamamoto, 1987). Similarly, most internal deletions or substitutions and point mutants eliminated or greatly decreased steroid binding (Giguere et al., 1986; Danielson et al., 1986). It thus appears that, aside from the few changes that are seen in rat vs human vs mouse receptors, the native sequence represents the optimal sequence for binding glucocorticoid steroids with high affinity and specificity. A 16 kDa steroid binding fragment of the rat glucocorticoid receptor has recently been identified (S. S. Simons et al., *J. Biol. Chem.* 264:14493-14497 (1989)). While this fragment retains the specificity of the intact 98 kDa receptor, and thus can be considered the core of the steroid binding domain, the affinity of this core fragment for glucocorticoid steroids is reduced by about a factor of 23 (Simons et al., 1989). Thus it would be predicted that almost any amino acid change in the 16 kDa core fragment would give rise to a loss of steroid binding, especially if the mutation was of a "crucial" amino acid.

There have been many efforts to identify the "crucial" amino acids involved in steroid binding to the glucocorticoid receptor. The initial candidates were cysteine (J. D. Baxter and G. M. Tomkins, *Proc. Natl. Acad. Sci. USA* 68: 932-937 (1971)) and lysine and arginine (D. M. DiSorbo et al., *Endocrinol* 106:922-929 (1980)). In fact, it has been known for many years that intact thiols are involved in the steroid binding of all receptors (R. J. B. King and W. I. P Mainwaring, "Steroid-Cell Interactions", University Park Press, Baltimore (1974)). Direct support for this conclusion was obtained when dexamethasone mesylate (Dex-Mes), a thiol-specific (S. S. Simons, *J. Biol. Chem.* 262:9669-9675 (1987)) affinity label for glucocorticoid receptors, was shown to covalently label just one thiol in the receptor, i.e., cysteine 656 (Simons et al., 1987). The identical cysteine in the mouse glucocorticoid receptor is also labeled by Dex-Mes (L. I. Smith et al., *Biochemistry* 27:3747-3753 (1988)). However, recent data indicate that at least 2 thiols are involved in steroid binding. In particular, the formation of an intramolecular disulfide in the steroid-free receptor molecule blocks steroid binding (N. R. Miller and S. S. Simons, *J. Biol. Chem.* 263:15217-15225 (1988); P. K. Chakraborti et al., *Endocrinology* 12:2530-2539 (1990)) and preincubation of unbound receptors with arsenite, which selectively reacts with closely spaced or vicinal dithiols, eliminates all steroid binding (S. S. Simons et al., *J. Biol. Chem.* 265:1938-1945 (1990); Lopez et al., 1990; Chakraborti et al., (1990)). Both thiols were found to be present in the 16 kDa core binding fragment (Chakraborti et al., 1990), which contains only 3 cysteines (Cys-640, -656, and -661). Recent results have identified the vicinal dithiols as being Cys-656 and -661. Thus these two thiols, and possibly Cys-640, would appear to be crucial for the high affinity and specificity of steroid binding to glucocorticoid receptors. Support for this conclusion comes from the facts that no other receptor has the same spacing of closely spaced thiols in the steroid binding domain and that arsenite, which selectively reacts with such closely spaced thiols, blocks the steroid binding activity of glucocorticoid receptors but not of any other steroid receptors (Lopez et al., 1990).

Based on the above information, it would be predicted that mutation of either Cys-656 or Cys-661 would both eliminate, or seriously reduce the affinity of, steroid binding to the glucocorticoid receptor and reduce the specificity of binding. As expected, cysteine-to-serine point mutations of Cys-640 and Cys-661 did cause a 3-4 fold reduction in affinity. However, the same mutation of Cys-656 caused a 3 fold increase in affinity. Even more unexpected was that the cysteine-to-glycine mutation of Cys-656 caused a greater increase in affinity that was accompanied by an increase in the specificity of steroid binding.

The present invention relates, in part, to novel glucocorticoid receptors with cysteine-to-glycine or -serine point mutations at the equivalent position of 656 in the rat receptor. Such super receptors represent improvements on nature that could not have been predicted based on previous work in the field. The present invention further relates to recombinant super glucocorticol receptors with an altered cysteine-to-glycine or serine change at the equivalent position of 656 in the rat receptor expressed in host cells.

SUMMARY OF THE INVENTION

It is an object of the present invention to provide a mammalian super glucocorticoid receptor that has a substitution at the equivalent position of cysteine 656 in the rat receptor by either glycine or serine.

It is another object of the present invention to provide a segment of DNA which encodes for the mammalian super glucocorticoid receptor wherein the DNA sequence encoding amino acid number 656 in rat corresponds to amino acid glycine or serine.

It is a further object of the present invention to provide a recombinant DNA molecule comprising a vector and a DNA segment which codes the super glucocorticoid receptor protein derived from mammals.

It is yet another object of the present invention to provide a host cell transiently or stably transformed or transfected with the above recombinant DNA molecule provided by this invention in a manner allowing expression of the protein encoded by the recombinant DNA molecule.

In another embodiment, the present invention relates to the recombinant super glucocorticoid receptor proteins expressed in the above host cells.

Another embodiment of the present invention relates to a method of treating a condition in a patient characterized by deficient or defective glucocorticoid receptors or decreased endogenous glucocorticoid steroid by administering to a patient by genetic engineering manipulations an altered (mutated) glucocorticoid receptor that has a higher affinity and specificity than the natural glucocorticoid receptor. The conditions include patients suffering from cortisol resistance, (Cushing's syndrome) and Addison's disease.

Various other objects and advantages of the present invention will become obvious from the drawings and the detailed description of the invention. The entire contents of all publications, mentioned herein are hereby incorporated by reference.

DETAILED DESCRIPTION OF THE INVENTION

Figure 1:
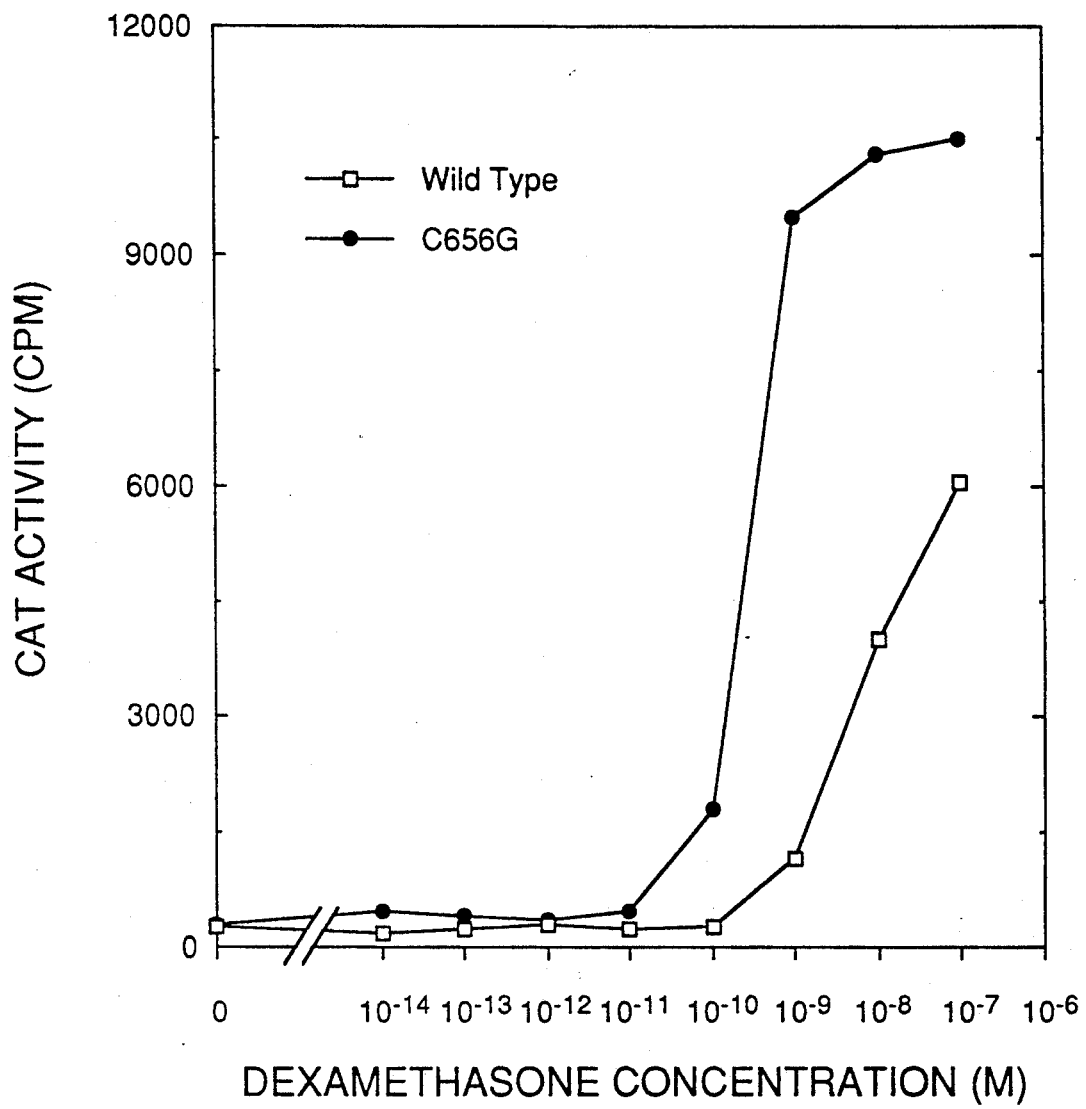
FIG. 1 shows a dose-response curve for Dex induction of reporter CAT gene by wild type and mutant receptors. The biological activity of wild type (□) or C656G mutant (▲) receptors was determined in CV-1 cells as described in the Example Section. The determined amounts of CAT activity from each plate were then plotted as a function of the concentration of dexamethasone added to each.

The present invention relates to novel glucocorticoid receptors in which the cysteine at the equivalent position 656 of the rat receptor has been substituted by either serine or glycine. The altered super receptor retains full biological activity in intact cells and has higher affinity and specificity for glucocorticoid steroid binding than the natural receptor. In particular, the present invention relates to novel glucocorticoid receptors containing point mutations at the equivalent position of 656 in rat receptors and the equivalent position in mouse (position 644) and human (position 638) receptors due to the dramatic conservation of properties and amino acid sequence (>88% homologous) in the receptors in human, rat and mouse. Furthermore, the steroid binding domain of the receptor, which is defined by the 250 carboxyl terminal amino acids of the protein, is >96% homologous in human, rat and mouse receptors. Thus the present invention includes novel altered glucocorticoid receptors at the equivalent position of cysteine-656 for rat in mammalians due to the extremely high homology found between them.

The present invention further relates to a DNA segment which encodes the altered glucocorticoid receptor protein described above wherein the nucleotide sequence of the altered DNA segment differs from the normal type sequence at the position corresponding to amino acid cysteine 656 of the rat receptor. The altered DNA sequence at this position encodes either glycine or serine resulting in a DNA segment which encodes the "super" receptor.

In another embodiment, the present invention relates to recombinant super glucocorticoid receptor proteins expressed through genetic engineering. The present invention also relates to recombinant DNA molecules and to host cells transformed therewith. The recombinant DNA molecule comprises a vector and the above-described DNA segment which encodes the altered mammalian glucocorticoid receptor. Possible vectors include mammalian expression vectors, for example, VARO and pSVL and other vectors known in the art that either transiently or stably transfect or transform host cells in a manner which allows expression of the "super" mammalian glucocorticoid receptor. Viral expression vectors derived from simian virus 40 (Elder et al., *Ann. Rev. Genet.* 15:295, (1981)), retrovirus (Eglitis and Anderson, *BioTechniques* 6:608, (1988)) and baculoviruses (Luckon and Summers, *BioTechnology* 6:47, (1988)) and a DNA segment encoding the altered glucocorticoid receptor may also be constructed without undue experimentation.

Examples of appropriate eukaryotic cells include, for example, Chinese hamster ovary (CHO) cells and simian CV-1 and COS cells that transiently or permanently express the altered protein.

Plasmid vectors comprising the DNA segment described above may also be constructed for production of protein in prokaryotic expression systems.

Genetic engineering offers the prospect of constructing new proteins that have more desireable properties than the naturally occurring proteins. A glucocorticoid receptor that has higher affinity and specificity than the natural receptor would be advantageous in several instances. Most importantly, it would permit the use of lower doses of glucocorticoids to affect maximal, receptor-mediated activity. This lower dose of steroid also means that there would be less binding of the glucocorticoid to other receptors and thus fewer side effects. In experiments with tissue culture cells and animals, these side effects are usually manifested as an uncertainly as to which receptor mediates the observed biological response. Stably transfecting the C656G receptor into tissue culture cells (or into animals by transgenics and genetic engineering) would permit one to use lower dosers of glucocorticoids to selectively recruit the mutant receptor in the presence of other receptors including the wild type glucocorticoid steroid (see FIG. 1). In people, the side effects of glucocorticoid therapy (such as osteoporosis and exacerbation of pre-existing cardiovascular or renal diseases (Williams and Dluhy, 1987), which may result, in part, from glucocorticoid binding to vitamin D and mineralocorticoid receptors respectively) have greater repercussions and can prevent initial or continued administration of the drug. Patients suffering from cortisol resistance due to defective glucocorticoid receptors (Chrousos et al., 1982; Nawata et al., 1987; Linder and Thompson, 1989) or requiring long term glucocorticoid therapy, such as Addison's disease where there is insufficient endogenous glucocorticoid steroid, would also benefit from a genetically engineered receptor such as the human equivalent of C656G since the lower doses of steroid required to activate the mutant receptor mean less cross-reactivity with other receptors. Second, any cell, animal, or patient containing the equivalent of the rat C656G glucocorticoid receptor (as opposed to the wild type receptor) will display a decreased absolute affinity for non-glucocorticoid steroids, which would result in fewer undesired glucocorticoid-like side effects upon administration of other steroids (e.g., aldosterone in patients being treated for hypoaldosteronism).

Certain aspects of the invention are described in greater detail in the non-limiting Examples that follow.

EXAMPLES

The following materials and procedures are referred to in the Examples that follow. Unless otherwise indicated, all operations were performed at 0° C.

Chemicals

Nonradioactive Dex (Sigma), [$^3$H]Dex (40 and 46 Ci/mmol, Amersham Corp.), and [$^3$H]Dex-Mes (44.7 Ci/mmol, DuPont-New England Nuclear) were commercially available. 3-([Tris-(hydroxymethyl)methyl]-amino)-propanesulfonic acid (TAPS) (Ultrol grade) was purchased from Behring Diagnostics. 4-Chloro-1-napthol was purchased from Sigma. Reagents for SDS-polyacrylamide gel electrophoresis, including Coomassie Blue R-250 and TWEEN 20, a non-ionic detergent, (EIA grade), were from Bio-Rad. Fluorescent "ELT-EMIT", a marking pen containing a fluorescent dye that is used to mark x-ray films used for fluorography, was from DuPont-New England Nuclear. ABC reagent for immunoperoxidase staining of Western blots was acquired from Vector Labs. All [$^3$H]labeled samples were counted in HYDROFLUOR, a liquid scintillation cocktail, (National Diagnostics) at 40–55% counting efficiency in a Beckman 5801 liquid scintillation counter with automatic cpm-to-dpm conversion.

Antibodies

The monoclonal anti-receptor antibody BUGR-2 (B. Gametchu and R. W. Harrison, *Endocrinol* 114:274–279 (1984)) and a polyclonal antibody (aPI) against the carboxyl terminal region of the rat glucocorticoid receptor (W. Hoeck et al., *J. Biol. Chem.* 264:14396–14402 (1989)) were used in the Examples described herein. Biotinylated anti-mouse and anti-rabbit second antibodies for Western blotting were purchased from Vector Labs.

Buffers and Solutions

TAPS buffer is composed of 25 mM TAPS, 1 mM ethylenediaminetetraacetic acid, and 10% glycerol. The pH of the TAPS buffer is adjusted to 8.2, 8.8, or 9.5 at 0° C. with sodium hydroxide. Two-fold concentrated SDS sample buffer (2×SDS) contains 0.6 M Tris (pH 8.85), 2% SDS, 0.2 M dithiothreitol, 20% glycerol, and bromphenol blue. Transfer buffer for Western blotting contains 25 mM Tris, 192 mM glycine, 20% methanol in water (pH ~8.3 at room temperature). Tris buffered saline (TBS) was 20 mM Tris and 0.28 M NaCl in water (pH =7.5 at room temperature).

Construction and identification of mutants

Single stranded DNA clones (in M13 mp18 and 19 [Amersham] or in pTZ18U [BioRad]) of the steroid binding domain fragment of the rat glucocorticoid receptor (SphI/EcoRI corresponding to amino acids 495 to 766) were annealed to each of the following synthetic oligonucleotides prepared by Synthecell (Rockville, Md.) (CCTGCTCTCCTTTGCTCCTG, CTCTACCCTCCATGTATGAC, CTCTACCCC GCATGTATGAC, and GTATGACCAATC TAAACAC; underlined base is different from the wild type sequence). Double stranded DNA was synthesized according to the Amersham site directed mutagenesis kit with nicking by NciI or PvuI, digestion with exoIII, and repolymerization. After transformation in TGI or MV1190, plaques or colonies were picked and analyzed for containing the desired mutation. Direct DNA sequencing and/or restriction enzyme analysis confirmed the presence of the desired base change. Double stranded DNA was prepared of these mutants and the SphI/EcoRl fragment was excised and subcloned into the mammalian expression vector (VARO) (D. Picard and K. R. Yamamoto, *EMBO J.* 6:3333-3340 (1987)). This vector was used for all experiments on the transient expression of biological activity. For the transient expression of the receptor protein, each mutant receptor (and the wild type receptor) was subcloned into a different mammalian expression vector (pSVL) (Miesfeld et al., 1986).

Growth and Transfection of Cells

Monolayer cultures of COS-7 cells were grown in DMEM (Gibco) supplemented with 5% fetal bovine serum (FBS) (Biofluids) at 37° C. in a 5% $CO_2$ incubator. Standard calcium phosphate transfection methods were used to introduce the wild type and mutant receptor expression vectors (pSVL) into COS-7 cells (100 mm plates [Costar] at a cell density of about $10^6$/plate were each treated with 10 μg of plasmid DNA). After ~16 hrs of incubation at 37° C. in a 5% $CO_2$ incubator, the excess calcium phosphate and precipitate were removed by washing with phosphate buffered saline (PBS). The cells were incubated at 37° C. for another ~48 hr in DMEM/ 5% FBS and harvested by trypsinization followed by centrifugation (for 10 min at 1570 ×g) and washing 3 times with PBS. The washed cells were stored at −80° C. until used.

Determination of biological activity of mutant receptors

Subconfluent cultures of CV-1 cells were co-transfected, using the standard calcium phosphate procedure, with 0.2 μg VARO receptor expression vector (containing the mutant receptor driven by the SV40 enhancer and the α-globulin promoter) and 1 μg G46TCO reporter vector (CAT gene driven by the thymidine kinase promoter [to −109 bp] and a 46 bp synthetic GRE derived from the murine mammary tumor virus long terminal repeat) for each 60 mm dish. Cells were incubated overnight at 37° C. in a 5% $CO_2$ incubator with the DNA precipitates, after which they were washed twice with PBS, and fresh medium (Dulbecco's modified Eagle's medium H-16 supplemented with 5% fetal calf serum) was added together with the indicated hormone.

After an additional 24 hr, at 37° C. in a 5% $CO_2$ incubator, extracts were prepared by four freeze-thaw cycles (−75° C., 65° C.) and centrifuged for 5 min at 15,000 xg. Heat-treated extracts (5 min, 65° C.) were normalized for protein content and the amount of expressed CAT enzyme activity was determined by a non-chromatographic assay (M. J. Sleigh, *Anal. Biochem.* 156:251-256 (1986)).

Preparation and Binding/Labeling of Receptors

COS-7 cell cytosol containing the steroid-free receptors was prepared by cell lysis at −80° C. and centrifugation at 15,000 ×g and labeled as described for HTC cells (S. S. Simons and P. A. Miller, *Biochem* 23:6876-6882 (1984)). Briefly, 30% cytosol solutions containing ~21 mM $Na_2MoO_4$ were prepared with three parts COS-7 cell cytosol, 2 parts pH 9.5 TAPS buffer, and 5 parts pH 8.8 TAPS buffer. The total EtOH in each experiment was kept constant and at a level of ≦1%. Steroid binding (or affinity labeling) was achieved by the addition of 20× stocks of [$^3$H]Dex ±550× nonradioactive Dex (final [$^3$H]Dex concentration =3-5 ×$10^{-8}$ M) or of [$^3$H]Dex-Mes±100× nonradioactive Dex (final [$^3$H]Dex-Mes concentration ~1.5×$10^{-7}$ M). After incubation for 2.5 hr, the [$^3$H]Dex-Mes-labeled solutions were quick-frozen at −78° C. for subsequent SDS-polyacrylamide gel electrophoresis analysis. The specifically bound [$^3$H]Dex was determined by first adding a 10% dextran-coated charcoal solution (added volume =20% of reaction solution volume) to remove free steroid and then subtracting the nonspecific binding seen in the presence of excess nonradioactive Dex.

Composition Binding Assay

Duplicate aliquots (72 μl) of COS-7 cell cytosol (33.5% in pH 8.8 TAPS/27 mM $Na_2MoO_4$ buffer) were treated with 4 μl each of [$^3$H]Dex (in pH 8.8 TAPS buffer) and various concentrations of non-radioactive competing steroid (in 20% EtOH in pH 8.8 TAPS buffer) (final concentration of [$^3$H]Dex ≈3 ×$10^{-8}$ M). The average specific binding was determined after 2.5 or 24 hr of incubation as described above, expressed as percentage of the non-competed control and plotted versus the $log_{10}$ of the concentration of the competing steroid. The Rodbard-corrected (D. Rodbard, Mathematics of hormone-receptor interaction. Steroid-receptor interactions. Receptors for Reproductive Hormones, B. W. O'Malley and A. R. Means, ed., (1973), 289-326, Plenum Press, New York, N.Y.) $K_a$, where the $K_a$ of dexamethasone =1, was determined from the concentration of non-radioactive steroid that caused 50% inhibition of [$^3$H]Dex binding.

Scatchard Analysis

Duplicate aliquots (76 μl) of COS-7 cell cytosol (31.6% in pH 8.8 TAPS/21 mM $Na_2MoO_4$ buffer) were incubated with 4 μl of [$^3$H]Dex ±500× non-radioactive Dex in pH 8.8 TAPS (final [$^3$H]Dex concentrations were 0.3-50×$10^{-9}$ M) for 24 hr before determining the average specific binding to receptors as described above.

Polyacrylamide Gel Electrophoresis

The preparation of samples for reducing SDS-polyacrylamide gels and the procedures for electrophoresis are as described (Simons, 1987). Constant percentage acrylamide gels (between 9 and 15% with a 1:40 ratio of bisacrylamide to acrylamide) were run in a water-cooled (15° C.) Protean II slab gel apparatus (Bio-Rad) at 30 mA/gel (25 mA/gel for 15% gels; 20 mA/gel while in the stacking gel for all gels). Gels were fixed and stained in 50% methanol, 7.5% acetic acid containing 0.01% Coomassie Blue R-250, destained in 10% methanol, 7.5% acetic acid, incubated for 1 hr in Enhance (Du Pont-New England Nuclear) and 30-60 min in 10% Carbowax PEG 8000 (Fisher) with constant shaking all at room temperature, dried on a Bio-Rad Model 443 gel drier at 60.C with a sheet of dialysis membrane backing (Bio-Rad) directly over the gel to prevent cracking, marked with Ult-Emit at the positions of the molecular weight markers (from Pharmacia P-L Biochemicals), and fluorographed for 7-12 days at −80° C. with Kodak X-OMAT XAR-5 film.

Western Blotting

The procedure used has been described elsewhere (Chakraborti et al., 1990). Briefly, the SDS-polyacrylamide gel was equilibrated in transfer buffer for at least 30 min at room temperature. Electrophoretic transfer to nitrocellulose was conducted in a well ventilated area (or at 4° C.) in a Transblot (BioRad) apparatus (~15 hr at 100 mA, then ~250 mA for 90 min). The nitrocellulose was stained with Ponceau S (0.02% Ponceau S and 0.04% glacial acetic acid in water) to visualize the transferred protein, incubated with blocking solution (2% Carnation non-fat dried milk in TBS) for 45 min, and washed with 0.1% Tween in TBS (TTBS) for 15 min, all at room temperature. Primary antibody (diluted 1:2000 [BUGR-2 acites fluid], 1:1000 [aPl], or 1:20 [BUGR-2 tissue culture medium] in TTBS) was added for ≧2 hr and then removed with 3 ×5 min washes of TTBS, all at room temperature. The incubation with biotinylated secondary antibody and the subsequent immunoperoxidase staining with ABC reagent were conducted as recommended by Vector Labs.

Example 1, Preparation and Expression of Point Mutations of Cys-640, -656, and -661

Site-directed mutagenesis with synthetic oligonucleotides of 19 or 20 bases in length were used to construct mutant steroid binding domain fragments of the rat glucocorticoid receptor (fragment is the SphI to EcoRI restriction enzyme digest of the intact receptor, corresponding to amino acids 495 to 766 of the rat receptor). A total of 4 mutant fragments were constructed: cysteine-to-serine for positions 640, 656, and 661 and cysteine-to-glycine for position 656.

The authenticity of each mutant fragment was determined either by restriction enzyme analysis or by direct nucleotide sequencing. These fragments were then used to replace the non-mutated SphI/EcoRI sequence of the intact receptor in a mammalian expression vector (VARO) (Picard and Yamamoto, 1987). In order to obtain high yields of transiently expressed wild type or mutant receptors in COS-7 cells, it was necessary to use a different vector. Thus the full length receptor was removed from the VARO vector with BamHI and inserted into the SVL vector (Miesfeld et al., 1986).

Further evidence that the desired point mutations had been effected was obtained by affinity labeling with [$^3$H]Dex-Mes (S. S. Simons and E. B. Thompson, Proc. Natl. Acad. Sci. 78:3541–3545 (1981)) each of the mutant receptors obtained in cell-free extracts of COS-7 cells that had been transiently transfected with the appropriate mutant receptor cDNA vector. After separation on SDS-polyacrylamide gels and visualization by fluorography, a specifically labeled band was seen for the 640 and 661 mutant receptors at the same molecular weight as for the wild type, 98 kDa receptor. In contrast, no specifically labeled species was seen for either of the 656 mutant receptors. This was not due to a lack of expression of the 656 mutant receptor, as shown both by a similar level of binding of [$^3$H]Dex and by comparable levels of receptor protein, as detected by Western blotting with anti-receptor antibodies (BUGR-2 [Gametchu and Harrison, 1984] and aP1 [Hoeck et al., 1989]).

These results argue that, at least for the 656 point mutations, the cysteine that is normally affinity labeled by Dex-Mes (S. S. Simons et al., J. Biol. Chem. 262:9676–9680 (1987)) has been replaced by another amino acid without any reduction in the size of the receptor.

Example 2, Steroid binding specificity of the mutant receptors

The specificity of steroid binding was determined by Rodbard correction (Rodbard, 1973) of the data from a competition binding assay (S. S. Simons et al., Biochem. Biophys. Res. Comm. 86:793–800 (1979); Miller and Simons, 1988). The initial data were collected from 2.5 hr binding assays because of concerns about the stability of the receptors over longer times.

The data Table 1A shows that there was almost no change in specificity after the mutation of Cys-640. Mutation of Cys-661 had little effect on the binding of RU 486 or cortisol but caused a 6 fold decreased affinity for 5α-dihydrotestosterone (DHT) and an approximately 10-fold decrease in the relative affinity of progesterone, aldosterone, and 17β-estradiol. The effect of mutating Cys-656 depends on the amino acid which is introduced. Replacement with glycine, to give the C656G receptor, produced much the same reduction in relative affinity for the same steroids as seen for C661S, except that there was less of an effect on aldosterone binding and no effect on cortisol binding. However replacement of Cys-656 with serine, to give the C656S receptor, causes a ≦3 fold reduction in relative affinity for progesterone, aldosterone, and 5α-DHT and a major reduction (≧10 fold) only for 17β-estradiol.

TABLE 1

| Steroid | SPECIFICITY OF STEROID BINDING TO MUTANT RECEPTORS | | | | |
|---|---|---|---|---|---|
| | Wild type | C640S | C656G | C656S | C661S |
| A.) 2.5 hr incubation: | | | | | |
| | Relative $K_d$ of Steroid Binding to Receptor (Mean + SD[n]) | | | | |
| RU486 | 3.4 ± 1.2(3) | 6.8 ± 2.2(3) | 2.5 ± 0.7(3) | 3.4 (2) | 3.84 ± 1.36(3) |
| Progesterone | 1.15 ± 0.32(4) | 1.21 ± 0.18(3) | 0.075 ± 0.014(4) | 0.72 (2) | 0.090 ± 0.032(3) |
| Cortisol | 0.92 ± 0.099(4) | 0.69 ± 0.08(3) | 1.17 ± 0.49(4) | 1.05 (2) | 0.32 ± 0.03(3) |
| Aldosterone | 0.22 ± 0.05(4) | 0.18 ± 0.002(3) | 0.060 ± 0.044(4) | 0.068 (2) | 0.016 ± 0.007(3) |
| 5α-DHT | 0.032 ± 0.003(3) | 0.020 ± 0.005(3) | 0.004 ± 0.001(3) | 0.0128 (2) | 0.005 ± 0.001(3) |
| 17β-Estradiol | 0.029 ± 0.006(3) | 0.010 ± 0.007(3) | 0.0017 ± 0.0006(3) | 0.0015 (2) | 0.0017 ± 0.0006(3) |
| B.) 24 hr incubation: | | | | | |
| | Relative $K_d$ of Steroid Binding to Receptor | | | | |
| Progesterone | 0.14 | | 0.0075 | | |
| Cortisol | 0.18 | | 0.33 | | |
| Aldosterone | 0.043 | | 0.0040 | | |

Competition binding experiments were performed in duplicate and analyzed as described in Example 2. The average values are listed along with the standard deviation (S. D.) when more than two experiments were performed. The number of experiments in section A are given in parentheses; all experiments in section B were performed twice.

Competition assays of short duration (e.g., 2.5 hr) often give the correct relative affinity values. However, since such short assays do not allow the binding of [$^3$H]Dex to reach equilibrium, inaccurate values are sometimes obtained (Simons et al., 1979; N. Lamontagne et al., Endocrinology 114:2252–2263 (1984)). When the specificity of the C656G receptor was reinvestigated in a 24 hr competition assay, the absolute values did change but the fold decrease in relative binding affinity, compared to the wild type receptor, actually increased somewhat. Thus, according to the longer competition assay, the C656G displays a 10-19 fold greater preference than the wild type receptor for the glucocorticoids cortisol and Dex vs the mineralocorticoid aldosterone and the progestin progesterone (Table 1B).

Example 3, Steroid binding affinity of the mutant receptors.

The results shown in Table 1 were unexpected in that none of the cysteine mutations had eliminated steroid binding. However, a reduction in the absolute affinity for [$^3$H]Dex was anticipated. Long term (24 hr) Scatchard analysis of each of the receptors was conducted to determine the change in affinity. Mutations of Cys-640 and -661 did produce a 3 to 4 fold decrease in affinity (Table 2). However, the two different mutations of Cys-656 resulted in a 3 and almost 9 fold increase in affinity.

With regard to C656G, it should be noted that this increased affinity does not entirely compensate for the decreased affinity of aldosterone and progesterone seen in Table 1B. Thus the absolute affinity of progesterone, and perhaps aldosterone, for the glucocorticoid receptor has decreased as a result of this mutation.

TABLE 2

| AFFINITY OF [$^3$H]DEX BINDING TO MT RECEPTORS | | |
|---|---|---|
| Receptor | $K_D (\times 10^{-9} M)$ | S. D. |
| Wild type | 4.73 | 2.04 |
| C640S | 13.1 | |
| G656G | 0.55 | 0.16 |
| C656S | 1.38 | 0.37 |
| C661S | 19.6 | |

Scatchard analyses were performed in duplicate as described in Example 2. The average $K_d$ values are listed. All values with S.D. are the result of three experiments; all other values are for two experiments.

Example 4, Biological Activity of the Mutant Receptors.

It is well known that the steroid binding of receptors can be dissociated from the ability to produce a biological response (Giguere et al., 1986; Rusconi and Yamamoto, 1987). In order to determine if either of the receptors that had been mutated at position 656 of the rat receptor were still biologically active, CV-1 cells were transiently transfected with both a mutant receptor expression vector and a vector containing a glucocorticoid-responsive reporter gene (G46tk/CAT). Each mutant receptor was found to be fully active (See FIG. 1 for data with C656G receptor).

As seen in FIG. 1, Dex induction of CAT activity with the C656G receptor occurs at ~10 fold lower concentrations than with the wild type receptor. This excellent correlation between the cell-free affinity of Dex for receptors and the concentration of Dex required to induce the biological response for the mutant vs wild type receptors argues that the mutation of an amino acid which is intimately involved in steroid binding (i.e., Cys-656) can give novel receptor molecules that are more selective and more responsive than the naturally occurring glucocorticoid receptors.

It is understood that the invention and the advantages and opportunities presented by it will be recognized from the above description which merely describes several preferred embodiments of the invention. It will be appreciated by one skilled in the art from a reading of this disclosure that various changes in form and detail can be made throughout without departing from the true scope of the invention and appended claims. Further, it will be recognized that the above-described invention has uses which are predicated on making advantageous use of the fact that the present invention may be applied to any method or therapy treatment which introduces proteins in a host cell or system that replaces normal proteins for those that might be an improvement on nature.

---

What is claimed is:

1. Mammalian super glucocorticoid receptor proteins wherein the equivalent position of cysteine 656 in SEQ ID NO. 5 is substituted for either glycine or serine.

2. The super glucocorticoid receptor according to claim 1 wherein the mammalian receptor is human.

3. A DNA segment encoding a mammalian super glucocorticoid receptor wherein the DNA sequence corresponding to cysteine 656 of SEQ ID NO. 5 is substituted by the DNA sequence of either glycine or serine.

4. A recombinant DNA construct comprising:
i) said DNA segment according to claim 3 and
(ii) a vector.

5. The DNA construct according to claim 4 wherein said vector is pSVL.

6. A host cell comprising said DNA construct according to claim 4.

7. The cell according to claim 6, wherein said host cell is a mammalian cell.

8. A recombinant super glucocorticoid receptor protein expressed in the host cell of claim 6.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

CCTGCTCTCC TTTGCTCCTG                      2 0

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:2:

CTCTACCCTC CATGTATGAC                                                                   20

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:3:

CTCTACCCGG CATGTATGAC                                                                   20

( 2 ) INFORMATION FOR SEQ ID NO:4:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:4:

GTATGACCAA TCTAAACAC                                                                    19

( 2 ) INFORMATION FOR SEQ ID NO:5:

( i ) SEQUENCE CHARACTERISTICS:
( A ) LENGTH: 795 amino acids
( B ) TYPE: amino acid
( D ) TOPOLOGY: linear ( x i ) SEQUENCE DESCRIPTION: SEQ ID NO:5:

| Met | Asp | Ser | Lys | Glu | Ser | Leu | Ala | Pro | Pro | Gly | Arg | Asp | Glu | Val | Pro |
| 1 |  |  |  | 5 |  |  |  |  | 10 |  |  |  |  | 15 |  |

| Gly | Ser | Leu | Leu | Gly | Gln | Gly | Arg | Gly | Ser | Val | Met | Asp | Phe | Tyr | Lys |
|  |  |  | 20 |  |  |  |  | 25 |  |  |  |  | 30 |  |  |

| Ser | Leu | Arg | Gly | Gly | Ala | Thr | Val | Lys | Val | Ser | Ala | Ser | Ser | Pro | Ser |
|  |  | 35 |  |  |  |  | 40 |  |  |  |  | 45 |  |  |  |

| Val | Ala | Ala | Ala | Ser | Gln | Ala | Asp | Ser | Lys | Gln | Gln | Arg | Ile | Leu | Leu |
|  | 50 |  |  |  |  | 55 |  |  |  |  |  | 60 |  |  |  |

| Asp | Phe | Ser | Lys | Gly | Ser | Thr | Ser | Asn | Val | Gln | Gln | Arg | Gln | Gln | Gln |
| 65 |  |  |  |  |  | 70 |  |  |  |  | 75 |  |  |  | 80 |

| Gln | Gln | Gln | Gln | Gln | Gln | Gln | Gln | Gln | Gln | Gln | Gln | Gln | Gln | Gln |
|  |  |  |  | 85 |  |  |  |  | 90 |  |  |  |  | 95 |

| Pro | Gly | Leu | Ser | Lys | Ala | Val | Ser | Leu | Ser | Met | Gly | Leu | Tyr | Met | Gly |
|  |  |  |  | 100 |  |  |  |  | 105 |  |  |  |  | 110 |  |

| Glu | Thr | Glu | Thr | Lys | Val | Met | Gly | Asn | Asp | Leu | Gly | Tyr | Pro | Gln | Gln |
|  |  |  | 115 |  |  |  |  | 120 |  |  |  |  | 125 |  |  |

| Gly | Gln | Leu | Gly | Leu | Ser | Ser | Gly | Glu | Thr | Asp | Phe | Arg | Leu | Leu | Glu |
|  |  | 130 |  |  |  |  | 135 |  |  |  |  | 140 |  |  |  |

| Glu | Ser | Ile | Ala | Asn | Leu | Asn | Arg | Ser | Thr | Ser | Val | Pro | Glu | Asn | Pro |
| 145 |  |  |  |  | 150 |  |  |  |  | 155 |  |  |  |  | 160 |

| Lys | Ser | Ser | Thr | Ser | Ala | Thr | Gly | Cys | Ala | Thr | Pro | Thr | Glu | Lys | Glu |
|  |  |  |  | 165 |  |  |  |  | 170 |  |  |  |  | 175 |  |

| Phe | Pro | Lys | Thr | His | Ser | Asp | Ala | Ser | Ser | Glu | Gln | Gln | Asn | Arg | Lys |
|  |  |  | 180 |  |  |  |  | 185 |  |  |  |  | 190 |  |  |

| Ser | Gln | Thr | Gly | Thr | Asn | Gly | Gly | Ser | Val | Lys | Leu | Tyr | Pro | Thr | Asp |
|  |  | 195 |  |  |  |  | 200 |  |  |  |  | 205 |  |  |  |

| Gln | Ser | Thr | Phe | Asp | Leu | Leu | Lys | Asp | Leu | Glu | Phe | Ser | Ala | Gly | Ser |
| 210 |  |  |  |  | 215 |  |  |  |  | 220 |  |  |  |  |  |

-continued

```
Pro  Ser  Lys  Asp  Thr  Asn  Glu  Ser  Pro  Trp  Arg  Ser  Asp  Leu  Leu  Ile
225                      230                      235                      240

Asp  Glu  Asn  Leu  Leu  Ser  Pro  Leu  Ala  Gly  Glu  Asp  Asp  Pro  Phe  Leu
                         245                      250                      255

Leu  Glu  Gly  Asn  Thr  Asn  Glu  Asp  Cys  Lys  Pro  Leu  Ile  Leu  Pro  Asp
                    260                      265                      270

Thr  Lys  Pro  Lys  Ile  Lys  Asp  Thr  Gly  Asp  Thr  Ile  Leu  Ser  Ser  Pro
               275                      280                      285

Ser  Ser  Val  Ala  Leu  Pro  Gln  Val  Lys  Thr  Glu  Lys  Asp  Asp  Phe  Ile
     290                      295                           300

Glu  Leu  Cys  Thr  Pro  Gly  Val  Ile  Lys  Gln  Glu  Lys  Leu  Gly  Pro  Val
305                      310                      315                      320

Tyr  Cys  Gln  Ala  Ser  Phe  Ser  Gly  Thr  Asn  Ile  Ile  Gly  Asn  Lys  Met
                    325                      330                      335

Ser  Ala  Ile  Ser  Val  His  Gly  Val  Ser  Thr  Ser  Gly  Gly  Gln  Met  Tyr
               340                      345                      350

His  Tyr  Asp  Met  Asn  Thr  Ala  Ser  Leu  Ser  Gln  Gln  Asp  Gln  Lys
          355                      360                      365

Pro  Val  Phe  Asn  Val  Ile  Pro  Pro  Ile  Pro  Val  Gly  Ser  Glu  Asn  Trp
     370                      375                      380

Asn  Arg  Cys  Gln  Gly  Ser  Gly  Glu  Asp  Ser  Leu  Thr  Ser  Leu  Gly  Ala
385                      390                      395                      400

Leu  Asn  Phe  Pro  Gly  Arg  Ser  Val  Phe  Ser  Asn  Gly  Tyr  Ser  Ser  Pro
                    405                      410                      415

Gly  Met  Arg  Pro  Asp  Val  Ser  Ser  Pro  Pro  Ser  Ser  Ser  Ser  Ala  Ala
               420                      425                      430

Thr  Gly  Pro  Pro  Pro  Lys  Leu  Cys  Leu  Val  Cys  Ser  Asp  Glu  Ala  Ser
               435                      440                      445

Gly  Cys  His  Tyr  Gly  Val  Leu  Thr  Cys  Gly  Ser  Cys  Lys  Val  Phe  Phe
     450                      455                      460

Lys  Arg  Ala  Val  Glu  Gly  Gln  His  Asn  Tyr  Leu  Cys  Ala  Gly  Arg  Asn
465                      470                      475                      480

Asp  Cys  Ile  Ile  Asp  Lys  Ile  Arg  Arg  Lys  Asn  Cys  Pro  Ala  Cys  Arg
                    485                      490                      495

Tyr  Arg  Lys  Cys  Leu  Gln  Ala  Gly  Met  Asn  Leu  Glu  Ala  Arg  Lys  Thr
               500                      505                      510

Lys  Lys  Lys  Ile  Lys  Gly  Ile  Gln  Gln  Ala  Thr  Ala  Gly  Val  Ser  Gln
          515                      520                      525

Asp  Thr  Ser  Glu  Asn  Pro  Asn  Lys  Thr  Ile  Val  Pro  Ala  Ala  Leu  Pro
     530                      535                      540

Gln  Leu  Thr  Pro  Thr  Leu  Val  Ser  Leu  Leu  Glu  Val  Ile  Glu  Pro  Glu
545                      550                      555                      560

Val  Leu  Tyr  Ala  Gly  Tyr  Asp  Ser  Ser  Val  Pro  Asp  Ser  Ala  Trp  Arg
                    565                      570                      575

Ile  Met  Thr  Thr  Leu  Asn  Met  Leu  Gly  Gly  Arg  Gln  Val  Ile  Ala  Ala
               580                      585                      590

Val  Lys  Trp  Ala  Lys  Ala  Ile  Leu  Gly  Leu  Arg  Asn  Leu  His  Leu  Asp
          595                      600                      605

Asp  Gln  Met  Thr  Leu  Leu  Gln  Tyr  Ser  Trp  Met  Phe  Leu  Met  Ala  Phe
     610                      615                      620

Ala  Leu  Gly  Trp  Arg  Ser  Tyr  Arg  Gln  Ser  Ser  Gly  Asn  Leu  Leu  Cys
625                      630                      635                      640

Phe  Ala  Pro  Asp  Leu  Ile  Ile  Asn  Glu  Gln  Arg  Met  Ser  Leu  Pro  Cys
                    645                      650                      655
```

| | | | | | | | | | | | | | | | |
|---|---|---|---|---|---|---|---|---|---|---|---|---|---|---|---|
| Met | Tyr | Asp | Gln 660 | Cys | Lys | His | Met | Leu 665 | Phe | Val | Ser | Ser 670 | Glu | Leu | Gln |
| Arg | Leu | Gln 675 | Val | Ser | Tyr | Glu | Glu 680 | Tyr | Leu | Cys | Met | Lys 685 | Thr | Leu | Leu |
| Leu | Leu 690 | Ser | Ser | Val | Pro | Lys 695 | Glu | Gly | Leu | Lys | Ser 700 | Gln | Glu | Leu | Phe |
| Asp 705 | Glu | Ile | Arg | Met | Thr 710 | Tyr | Ile | Lys | Glu | Leu 715 | Gly | Lys | Ala | Ile | Val 720 |
| Lys | Arg | Glu | Gly | Asn 725 | Ser | Ser | Gln | Asn | Trp 730 | Gln | Arg | Phe | Tyr | Gln 735 | Leu |
| Thr | Lys | Leu | Leu 740 | Asp | Ser | Met | His | Glu 745 | Val | Val | Glu | Asn 750 | Leu | Leu | Thr |
| Tyr | Cys | Phe 755 | Gln | Thr | Phe | Leu | Asp 760 | Lys | Thr | Met | Ser | Ile 765 | Glu | Phe | Pro |
| Glu | Met 770 | Leu | Ala | Glu | Ile | Ile 775 | Thr | Asn | Gln | Ile | Pro 780 | Lys | Tyr | Ser | Asn |
| Gly 785 | Asn | Ile | Lys | Lys | Leu 790 | Leu | Phe | His | Gln | Lys 795 | | | | | |